(12) United States Patent
Elaissari et al.

(10) Patent No.: US 6,521,341 B1
(45) Date of Patent: Feb. 18, 2003

(54) MAGNETIC PARTICLES, METHOD FOR OBTAINING SAME AND USES FOR SEPARATING MOLECULES

(75) Inventors: Abdelhamid Elaissari, Lyons (FR); Christian Pichot, Corbas (FR); Bernard Mandrand, Villeurbanne (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/582,352

(22) PCT Filed: Jan. 6, 1999

(86) PCT No.: PCT/FR99/00011

§ 371 (c)(1),
(2), (4) Date: Sep. 21, 2000

(87) PCT Pub. No.: WO99/35500

PCT Pub. Date: Jul. 15, 1999

(30) Foreign Application Priority Data

Jan. 6, 1998 (FR) .............................. 98 00220

(51) Int. Cl.[7] .................................. G11B 5/16
(52) U.S. Cl. ............. 428/403; 428/407; 428/694 BA; 428/900; 427/128; 427/129; 427/130; 427/131
(58) Field of Search .................. 428/403, 900, 428/407, 694 BA; 427/128–131

(56) References Cited

FOREIGN PATENT DOCUMENTS

| EP | 0 390 634 A | 10/1990 |
|---|---|---|
| EP | 0 585 868 A | 3/1994 |
| EP | 0 666 577 A | 8/1995 |
| EP | 0 709 680 A | 5/1996 |
| WO | WO 83/03920 | 11/1983 |
| WO | WO 90/06045 | 6/1990 |
| WO | WO 94 09368 A | 4/1994 |
| WO | 97/45202 | * 12/1997 |
| WO | WO 97 45202 A | 12/1997 |

OTHER PUBLICATIONS

Kondo, et al. "Development and Application . . . " Applied Microbiology and Biotechnology, vol. 41, 1994 pp. 99–105, XP 000613881.*

Kondo et al., *Development and Application of Thermo–Sensitive Magnetic Immunomicrospheres for Antibody Purification*, Applied Microbiology and Biotechnology, vol. 41, 1994, pp. 99–105, XP000613881.

* cited by examiner

Primary Examiner—Leszek Kiliman
(74) Attorney, Agent, or Firm—Oliff & Berridge, PLC

(57) ABSTRACT

The invention concerns magnetic and heat-sensitive particles having a predetermined size between 0.05 and 10 $\mu$m, each particle comprising: an inner composite core consisting of a solid organic or inorganic particle, containing within it a magnetic filler; an outer coati based on a polymer capable of interacting with at least a biological molecule, the outer polymer is heat-sensitive and has a predetermined low critical solubility temperature (LCST) ranging between 10 and 100° C. and preferably between 20 and 60° C. The invention also concerns methods for obtaining said particles and their uses. The particles are characterized in that there is an intermediate layer between the inner core and the outer layer isolating said inner core magnetic filler with respect to said functionalized outer layer. Said invention is particularly useful for separating proteins and/or nucleic acids.

28 Claims, 4 Drawing Sheets

MAGNETIC PARTICLES, METHOD FOR OBTAINING SAME AND USES FOR SEPARATING MOLECULES

Figure 1:
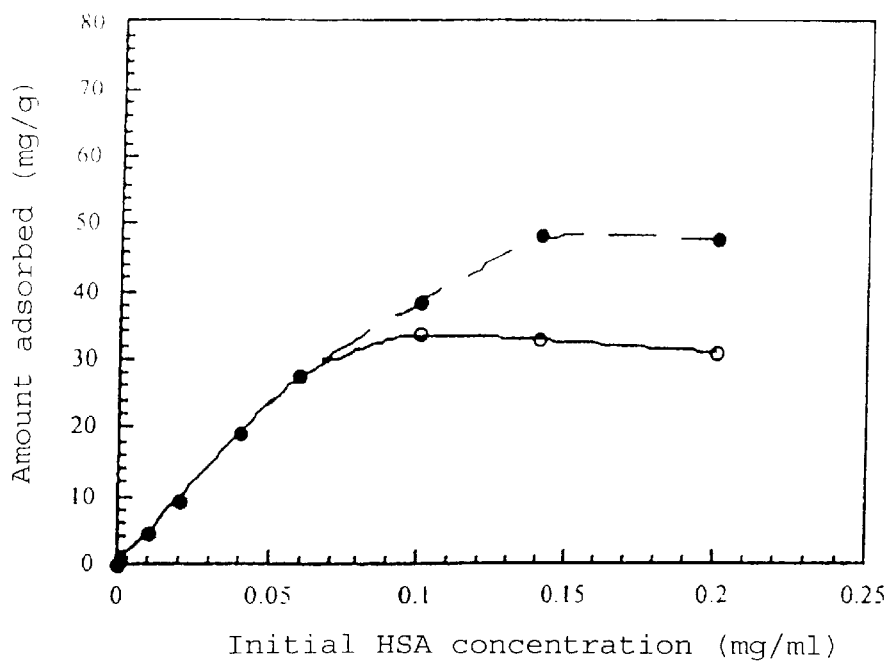

The present invention concerns heat-sensitive magnetic particles having a predetermined size between 0.05 and 10 µm, which comprises, on the one hand, an internal composite core and, on the other hand, an external layer based on a polymer which is capable of interacting with at least one biological molecule. The invention also concerns production methods and uses of such particles.

In the following account, the term "composite" is synonymous with a magnetic compound which is simple, such as ferrite, or complex, such as ferrite distributed, incorporated or coated in a polymer matrix.

This internal composite core may have a diameter between 20 nm and 10 µm.

Biological diagnosis consists in detecting a disease using the analysis of biological samples (urine, blood, cerebrospinal fluid, sediment, sputum, etc.). In the research context, it is desirable in particular to be able to extract and concentrate, under conditions compatible with the activity assays of certain proteins or nucleic acids, in order to demonstrate the presence, in people who are ill, of a specific protein or DNA or RNA sequence. In the case of proteins, the methods currently used consist in introducing into the medium a large amount of salts which bring about the precipitation of the proteins, and then in separating proteins and salts by centrifugation. However, these methods are very laborious and, in addition, the proteins thus extracted are often denatured, i.e. they have lost their biological properties. This explains the interest which has been shown, in recent years, in magnetic latexes in the biomedical field.

Specifically, the polymer supports in the form of latex are extensively used because they exhibit many advantages, in particular that of offering a large specific surface area (several tens of $m^2$) per gram of particle.

The prior art can be defined by documents EP-A-0,106,873 and EP-A-0,446,260, which describe superparamagnetic monodisperse particles comprising a polystyrene/divinylbenzene copolymer-based porous core into which grains of magnetic iron oxide are incorporated, and a functionalized external layer which is capable of interacting with nucleic acid probes.

According to the method for preparing particles described in these documents, the magnetic iron oxides are incorporated by precipitation of the corresponding salts, which limits the proportion of magnetic filler incorporated, and makes it possible to obtain the magnetic filler only in a surface monolayer, which can induce phenomena of inhibition of biomolecule activity.

Similarly, document EP-A-0,585,868 describes magnetic particles consisting of a core based on a first polymer and on a magnetic layer covering the core consisting of a second polymer in which is distributed the ferrite-based magnetic material, and which is capable of interacting with an antigen or an antibody, the magnetic material being deposited by precipitation of the iron salts.

The incorporated magnetic material is directly exposed to the subsequent treatments of the particles, and a loss of the filler ensues during the use of the particles, which can cause problems in particular of enzymatic inhibition and of denaturation of biological entities.

The subject of document WO-A-94/09368 is the use of gelatin in place of the polymer based on acrylamine derivatives, as we recommend. This document proposes however a crosslinking agent.

Even so, gelatin has functions which are totally different from those of a polymer as claimed. Thus, gelatin is absolutely not heat-sensitive, and it was not at all proven that the crosslinking of heat-sensitive acrylamine derivatives leads to the trapping of the magnetic inclusions present in the internal core.

According to the article by A. Kondo, (A. Kondo, H. Kamura and K. Higashitani (1994) *Appl. Microbiol, Biotechnol.*, 41, 99–105) a method for obtaining magnetic particles is known which comprises a core which is based on a first polymer consisting of a polystyrene, and in which is distributed a magnetic material, and a hydrophilic layer covering the core which is based on a heat-sensitive polymer consisting of poly(N-isoproprylacrylamide). The method described comprises the following two steps. According to a first step for obtaining the magnetic core, the magnetic material is brought into contact with the styrene in the presence of a polymerization initiator. According to a second step for obtaining the hydrophilic layer, the core obtained is brought into contact with N-isoproprylacrylamide and methacrylic acid, in the presence of the above polymerization initiator. Bovine serum albumin is bound to the particles thus obtained in order to subsequently isolate antibodies directed against bovine serum albumin, present in a sample.

This document proposes magnetic particles which comprise inclusions of magnetic material present in the internal core and/or in the external layer. Of course, if said external layer comprises inclusions, they might be released into the reaction medium and prejudice possible applications and uses in the biological and/or diagnostic field requiring specific reactions. Moreover, there is no use of crosslinking agent, and thus no formation of an intermediate layer. If such particles are put together with a solvent, the inclusions will be liberated into the reaction medium, even if these inclusions are present only in the internal core. In addition, said particles are effective only for proteins. The separation of nucleic acids cannot be envisaged.

Thus, to ensure as efficient a separation as possible of these particles in the sample, the applicants have employed thermoflocculation in which the temperature of the sample is increased, this having the effect of completing the action of a magnetic field. It is document WO-A-97/45202 which proposes particles which are superparamagnetic, and which have a very homogeneously distributed magnetic filler, the proportion of which can vary between 1 and 80%, in particular from 25 and 80% by weight with respect to the polymer(s) constituting the particles. The present invention makes it possible to reach high proportions of incorporated magnetic filler, in particular since the method employed makes it possible to distribute the magnetic filler in the form of multilayers. A considerable advantage results therefrom, i.e. the possibility of efficiently separating, from the sample, the particles of the invention, without having to resort to the combined action of another separation technique such as flocculation.

This invention has an objective which is different from that of the present invention. In addition, there is a magnetic internal layer which covers a core which is not magnetic. Moreover, the absence of an intermediate layer is noted. This configuration does not prevent the release of magnetic inclusions from the internal layer into the reaction medium.

While these particles satisfy most of the expectations of the biologists, they comprise a certain number of drawbacks. Thus, these particles do not make it possible to separate, firstly, proteins from nucleic acids, which may be particularly valuable depending on the work undertaken (identification of antibodies, amplification of sequences, etc.) and secondly, nucleic acids. Thus, in the case of nucleic acid separation, the particles according to the invention do not inhibit the various amplification techniques which may be used (PCR, NASBA or TMA). Finally, it is not absolutely necessary to release the extracted substances (proteins or nucleic acids)—with respect to the particles, the identification or amplification assays can be carried out directly after the magnetic separation.

To this effect, the present invention concerns heat-sensitive magnetic particles having a predetermined size between 0.05 and 10 µm, each particle comprises:

an internal composite core which consists of a solid organic or inorganic particle, and which contains within itself a magnetic filler, and an external layer based on a polymer which is capable of interacting with at least one biological molecule, the external polymer is heat-sensitive and has a predetermined lower critical solubility temperature (LCST) between 10 and 100° C., and preferably between 20 and 60° C., characterized in that an intermediate layer is present between the internal core and the external layer, which isolates the magnetic filler of said internal core with respect to said functionalized external layer.

According to a preferential embodiment, the intermediate layer consists of at least:

one functional or nonfunctional monomer, which is able to polymerize in order to give a polymer, and one crosslinking agent.

According to another preferential embodiment, the external layer consists of at least:

one functional monomer, which is able to polymerize in order to give a polymer, and one initiator.

According to one embodiment variant, the functional monomer consists of a cationic monomer such as 2-aminoethyl methacrylate chloride.

According to another embodiment variant, the functional monomer consists of an anionic monomer such as a carboxylic or sulphate monomer.

Whatever the embodiment or embodiment variant, the polymer consists of hydrophilic polymers, in particular the acrylamine derivatives, and preferably poly(NIPAM) obtained by polymerization of N-isopropylacrylamine (NIPAM).

According to the first preferential embodiment, the crosslinking agent consists of N,N'-methylenebisacrylamide.

According to the second preferential embodiment, the initiator consists of at least one cationic initiator such as azobis(2-amidinopropane)chloride.

Still according to the second preferential embodiment, the initiator consists of at least one anionic initiator such as potassium persulphate.

In all scenarios, the external layer is functionalized with a protonated amine or amidine group.

The external layer is functionalized with a carboxylic or sulphate group.

The present invention also concerns a method for obtaining particles as defined above, which consists in bringing together and in reacting:

a composite core which consists of a solid organic or inorganic particle, and which contains within itself a magnetic filler, a functional or nonfunctional monomer, which is able to polymerize in order to give a polymer, and a crosslinking agent, until the composite core, constituting the internal core, is encapsulated and isolated by a mixture of polymer and crosslinking agent, and until an external layer based on the polymer which is capable of interacting with at least one biological molecule is formed.

According to a preferential embodiment, the cationic magnetic particles are prepared by encapsulation by polymerization, on composite cores, of the water-soluble monomers of acrylamide and/or of acrylamide derivatives in the presence of azobis (2-amidinopropane)chloride.

Advantageously, the polymerization is performed in the presence of N,N'-methylenebisacrylamide and/or of 2-aminoethyl methacrylate chloride.

According to another preferential embodiment, the anionic magnetic particles are prepared by encapsulation by polymerization, on composite cores, of the water-soluble monomers of acrylamide or of acrylamide derivatives in the presence of potassium persulphate.

Advantageously, the polymerization is performed in the presence of N,N'-methylenebisacrylamide and/or of carboxylic monomers.

Whatever the method used, prior to the polymerization, the magnetic particles obtained by adsorption or polymerization are covered with at least one substance which isolates the magnetic filler, such as polystyrene and/or methyl polymethacrylate.

Preferably, the method consists in using the reagents in a proportion of:

10 to 30% of water-soluble monomer of acrylamide or of an acrylamide derivative, at most 10% of at least one crosslinking agent, and 1 to 5% of at least one stabilizer, with respect to the total mass of the particle obtained by the method.

The invention also concerns the use of cationic particles as described above to immobilize or extract nucleic acids or any polyelectrolytic entities, and to release and/or analyse, after magnetic separation, said nucleic acids or entities, the temperature of use being constantly lower than the LCST.

The invention finally concerns the use of anionic particles as described above to extract proteins by binding to the particles when the temperature is higher than the LCST, and to release and/or analyse, after magnetic separation, said proteins when the temperature is lower than the LCST.

I—Encapsulation of the Commercial Magnetic Particles or Composite Cores

Many magnetic particles are sold. The surface of these particles is anionic or cationic. Conversely, their composition is never detailed. These particles possess a variable polymolecularity index. Specifically, the Seradyn, Spherotec and Dynal particles are monodisperse, whereas those from Estapor, although having an average diameter of 1 m, are very polydisperse.

All these particles have been tested in the nucleic acid amplification methods, and they create inhibition reactions. It is thus necessary to modify their surface in order to be able to work on nucleic acids.

A/ Preparation of the Cationic Hydrophilic Magnetic Latex

The encapsulation reactions were carried out under nitrogen atmosphere and at 70° C.

1 g of seed particles was diluted with 40 ml of milliQ water preheated to boiling and degassed under nitrogen.

The styrene was added simply when the seed particles were hydrophobic. It was added alone, before the start of synthesis, and left for a certain time, for example between 30 and 60 minutes, in contact with the magnetic composite core.

The monomers were introduced in the following proportions:

NIPAM: 0.3254 g, i.e. 32.5%/seed (80%/polymer if the seed contains 60% of ferrite),
MBA: 0.0274 g, i.e. 6.18 mol %/NIPAM,
AEM: 0.0740 g, i.e. 15.5 mol %/NIPAM, and
V50: 0.0061 g, i.e. 0.80 mol %/NIPAM.

It is necessary to add a surfactant, for example 0.14 g of triton X405.

The initiator is introduced with 1 ml of water. The monomers are subsequently added. They are diluted in 9 ml, and they are introduced progressively into the reactor, i.e. over a 15-minute period of time, or they are introduced all in one go as soon as the initiator is added.

In the context of the present invention, Estapor composite cores were encapsulated. Anionic particles (EM1 100/20 and EM1 100/30 particles) and cationic particles (R95-07 particles) were used.

The particles prepared from the EM1 100/20 and EM1 100/30 latexes made it possible to obtain a filler density between 50 and 300 millimoles of $NH_2$ (mmol $NH_2$) per gram of latex, depending on the polymerization method used (closed reactor, deferred or continuous addition).

The particles prepared from the R95-07 latex made it possible to obtain a filler density between 50 and 300 mmol $NH_2$ per gram of latex, depending on the polymerization method.

According to the protocol for adding the monomers into the reaction system, several polymerization methods may be differentiated.

1—Closed-reactor Polymerization Termed "Batch"

Before the start of the reaction, the monomers are introduced into the reactor with the other ingredients and without subsequent addition.

Because of the difference in reactivity of the monomers, this method often leads to the appearance of a drift in composition. This reveals itself by the production of macromolecules having compositions which vary considerably as a function of the conversion. This method proves to be relatively inefficient for surface incorporation, since a considerable portion of the functional monomer risks being lost either inside the particles, or in the form of water-soluble polymer. When the copolymerization is performed by "batch" with monomers of polar nature, smaller particles are obtained, in large number, but with a limited conversion. This behaviour is linked to the considerable solubility in water of these monomers, and it is attributed to the preponderance of the homogeneous nucleation mechanism.

2—Semicontinuous Polymerization

A portion at least of the monomers is introduced into the reactor over a period between the start of the reaction and its end. This adding can be performed at a fixed rate or following a given profile. The aim is to control the addition of the monomer mixture in such a way as to obtain a copolymer of controlled composition; it is in this way that addition conditions are often obtained such that the rate of polymerization is faster than that of addition. This makes it possible to obtain copolymers with homogeneous composition.

3—Polymerization by Deferred Addition Termed "Shot"

During a copolymerization, and once the reaction is in progress, the functional monomer alone, or in the presence of the basic monomer, is introduced into the system in a controlled way. The success of the manipulation thus depends on the degree of prior knowledge of the kinetics of copolymerization. It is an efficient method for promoting the surface incorporation. The selection of the experimental conditions (degree of conversion at the time of addition, composition and concentration of the monomer mixture) makes it possible to optimize the surface yields.

4—Polymerization on Seed

It consists in introducing the functional monomer into the system containing a latex which is already constituted and completely characterized. The functional monomer can be added pure or in a mixture with the basic monomer of the seed, in one step or semicontinuously.

Among the abovementioned various polymerization techniques, only the closed-reactor polymerization and the polymerization on seed were used.

B/ Preparation of the Anionic Hydrophilic Magnetic Latex

The latexes used consist of a core of polystyrene and/or ferrite, which confers upon them magnetic properties. They are also covered, by polymerization, with N-isopropylacrylamide (NIPAM). A crosslinker, N,N'-methylenebisacrylamide (MBA), is added. The initiator used is potassium persulphate ($K_2S_2O_8$), which explains the presence of sulphate groups on the surface of the latex, and thus its anionic nature.

II—Nucleic Acid Separation

The purpose of this invention is to develop a novel diagnosis test model, which should make it possible to detect, very early on, the presence of infectious genes in an individual. It involves establishing a protocol for specifically extracting DNAs or RNAs in a way as to be able to assay them, while at the same time having previously removed the proteins which are present in large amounts in the sampling medium. The support chosen should, in a first step, not induce a reaction which inhibits the amplification methods for DNAs and for RNAs such as PCR, NASBA or TMA. This step being positive, the support will have to be capable of specifically isolating nucleic acids in sufficient amount.

The support should thus be hydrophilic, and should not release substances which inhibit amplification reactions.

This study consists in obtaining cationic magnetic latexes covered with a hydrophilic furry coat which consists of N-isopropylacrylamide (NIPAM), and is functionalized with 2-aminoethyl methacrylate (AEM) chloride.

The surface of the commercial particles or composite cores was modified, and the cores or particles were encapsulated. The principal particles available are the particles from Dynal, Seradyn, BioMag, Spherotec or Estapor (trademarks).

Patent Application FR96/04691, filed on Apr. 9 1996 by the applicant, concerns such a nucleic acid separation. Its content is thus integrated into the present patent application.

III—Protein Separation

The advantage of the latexes is that they are not only heat-sensitive, but also magnetic, which makes it possible to avoid the centrifugation steps. A simple laboratory magnet makes it possible to separate the magnetic particles from the rest of the medium. This technique thus has the advantage of being faster and more easily automated with a view to a possible industrial use.

Firstly, it is necessary to optimize the physiochemical conditions for concentrating solutions containing human albumin (HSA: human serum albumin) which is a model protein. Secondly, the conditions must be found which make it possible to concentrate all the proteins present in the urine.

The tests on solutions prepared from HSA alone were carried out using an EM1 070/60 core, whereas the applications on the urine were carried out with an EM1 100/20 core.

After washing the composite cores with boiled degassed milliQ water under nitrogen for 1 hour, 1 g of Estapor latex in solution in 40 cm$^3$ of water is introduced into the reactor, which is kept at 70° C. and under a flow of nitrogen throughout the experiment. After adding 200 ml of styrene, it is left to swell for 2 hours.

0.0061 g of KPS is dissolved in 1 ml of water. Then, every minute, 1 ml of a solution of 0.325 g of NIPAM, 0.027 g of MBA and 0.14 g of triton (X-405) is added to 9 ml of water; this mixture is left to stir for at least 10 hours.

Washing of the latex is then carried out.

The aim of this procedure is to remove the surfactant, as well as the electrolytes and the polymer chains free in solution. Specifically, the surfactant may lead to disruption of the Bradford reagent (chemical method used to assay proteins), and may decrease the adsorption capacities of the latexes.

Since the latex used is magnetic, it is very easy, using a magnet, to remove the supernatant, to replace it with freshly exchanged milliQ water, and then to vigorously stir it using a vortex. This washing is repeated until the supernatant is clear (it is also possible to verify that the conductivity of the latex after the final wash is practically as low as the conductivity of the milliQ water ($\approx$0.02 mS)).

A/ Human Serum Albumin (HSA)

HSA is a model protein for studying various parameters, such as pH or ionic force, which make it possible to concentrate the protein to a maximum.

It is an ellipsoidal protein of approximate dimensions 4×4×14 nm and of molecular weight in the vicinity of 62,000 g/mol.

Its zeta potential (physicochemical measurement relating to the charge density at the surface of the particle) varies with the pH: the HSA protein is cationic for pH<PI (isoelectric point: pH value at which the net charge is zero; PI=4.8 for HSA) and anionic for pH>PI.

B/ Methods for Measuring the Protein Concentration

The assaying of proteins, for example HSA, is carried out using the Bradford reagent. This assay is possible through the use of Coomassie blue (G 250), which forms a complex with the proteins (initially brown, it turns a blue colour which gets deeper as the protein concentration increases). The protein/dye complex has a very high extinction coefficient, which makes it possible to have a very sensitive method. In addition, the coloration is virtually instantaneous, which allows rapid assaying.

All the Bradford assays are carried out under the same conditions: 15 µl of the solution the determination of whose protein concentration is desired +135 µl of appropriate buffer (desired pH and ionic strength)

+150 µl of Coomassie reagent.

1—Determination of the Amount Adsorbed

The amount of protein adsorbed Ns is given by the following formula:

$$Ns\ (mg.g^{-1}) = V(C_i - C_f)/m$$

with:

$C_i$ (mg/ml)=initial protein concentration of the solution in contact with the latex;

$C_f$=final HSA concentration in the supernatant after adsorption;

V (ml)=total volume of the solution;

m (g)=mass of latex in the solution.

2—Determination of the Amount Desorbed

If the proteins were initially adsorbed onto a mass m (in g) of latex, and if, after desorption in a volume V (ml), a protein concentration C (mg.ml-1) is determined by Bradford assay, then the amount desorbed is given by:

$$Ns\ (mg.g^{-1}) = V*C/m$$

C/ Optimization of Parameters

1—Adsorption of the HSA Protein

In this part, the values are determined for the pH, the ionic strength and the temperature for adsorbing the maximum of proteins onto the latex particles.

a. Procedure

The experiments are carried out in eppendorf tubes (maximum content: 1.5 ml).

Volume of latex: 100 µl (i.e. 2.1 mg)

Volume of the HSA solution: 200 µl (variable mass)

Volume of buffer: 700 µl

Given that 0.2 ml of HSA solution of given concentration is introduced for a total volume of 1 ml, the real concentration of the HSA solution in contact with the latex is obtained after correction by a dilution factor of 0.2.

b. Influence of the Temperature

The influence of the temperature on the adsorption is notable, independently of the pH. FIG. 1 shows the variation in the amount of proteins adsorbed as a function of the initial protein concentration, at two different temperatures, for a pH=4.7 and an ionic strength of 0.01 mol/l.

The same tendency is observed at pH 5.7 (at 20° C., the adsorption is 30% lower than at 40° C.) and at pH 8.6.

Since only the hydrophilic/hydrophobic nature of the latex varies with the temperature, this study makes it possible to demonstrate the influence of the hydrophobic interactions on the adsorption.

The fact that the curves are merged for the first points may be due to the procedure. To test the adsorption at 40° C., latex, proteins and buffer were mixed at room temperature, and then heated to 40° C. It may be therefore that, for the low HSA concentrations, whereas adsorption is thought to be taking place at 40° C., the proteins are adsorbed onto the latex in its hydrated form since T<32° C.

c. Influence of the Time of Adsorption

Figure 2:
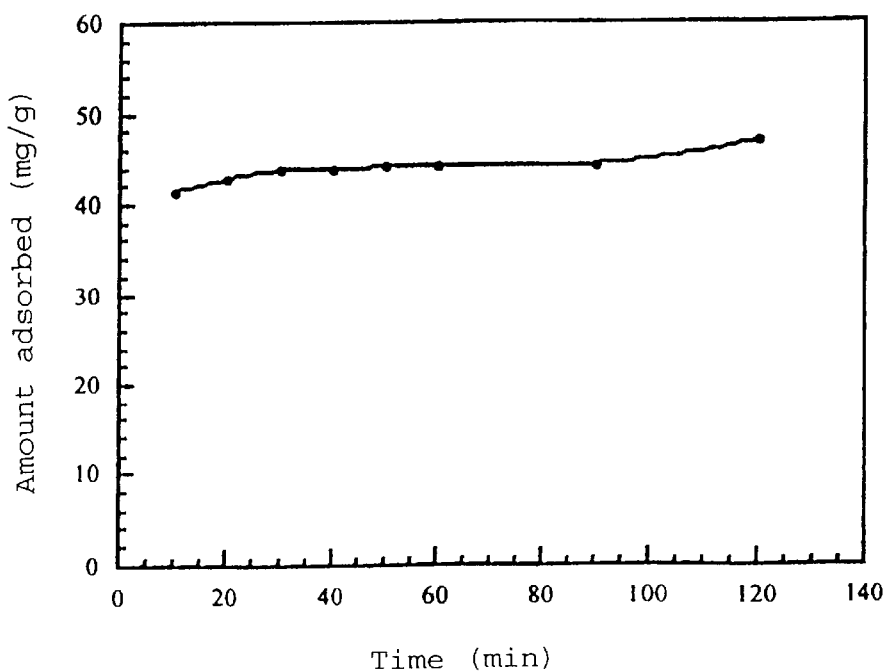

Under the conditions judged to be optimal for the adsorption, a kinetic study is carried out of the amount adsorbed as a function of the incubation time. FIG. 2 shows that, after 30 minutes, practically the maximum possible amount has already been adsorbed.

d. Influence of the pH

The adsorption was carried out for the pHs 4.7, 5.7 and 8.6, for HSA concentrations between 0 and 0.2 g.l$^{-1}$. For the adsorption at pH=8.6, the curve cannot be drawn for (HSA) >0.06 g.$^{-1}$ because, the amount adsorbed being very low, ($C_i-C_f$) is virtually zero, and the measuring method is not precise enough to detect this small variation.

Figure 3:
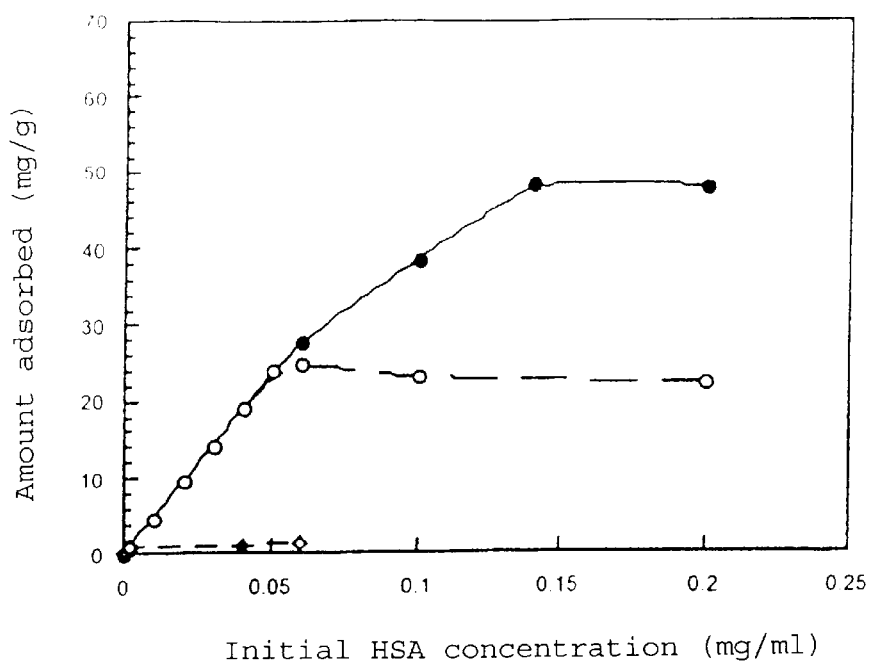

By superimposing the three curves obtained, the graph in FIG. 3 is obtained, which demonstrates:

i) the existence of a plateau for an adsorption of 50 mg of proteins per g of latex (saturation of the adsorption sites);

ii) a maximum adsorption for pH=4.7.

This result is in agreement with the influence of the electrostatic interactions: for pH<PI, the protein is cationic and the latex anionic, hence an electrostatic attraction and a favoured adsorption, whereas for pH>PI, the protein and the latex are anionic, hence an electrostatic repulsion which decreases the amount of HSA adsorbed. This study thus demonstrates the influence of the electrostatic forces on the adsorption.

e. Influence of the Ionic Strength

Figure 4:
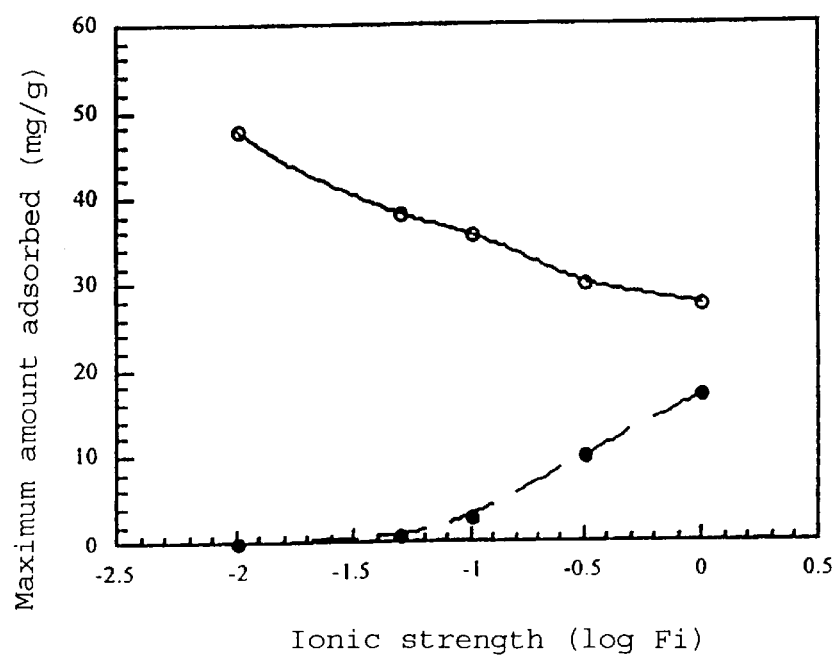

The curves giving the amount adsorbed as a function of the ionic strength, for the same initial protein concentration, are reproduced in FIG. 4.

i) pH=4.7 and (HSA)=0.14 mg.ml$^{-1}$ and T=40° C.

This curve shows that the adsorption is maximal for a low ionic strength; this is in agreement with attractive electrostatic interactions, which promote the adsorption all the more as they are less screened as the salinity of the medium decreases.

ii) pH=8.6 and (HSA)=0.04 mg.ml$^{-1}$ and T=40° C.

This curve shows that the adsorption is maximal for a high ionic strength; at basic pH, the electrostatic interactions are repulsive, thus the adsorption is greater as these interactions are screened.

f. Influence of the Amount of Latex

Figure 5:
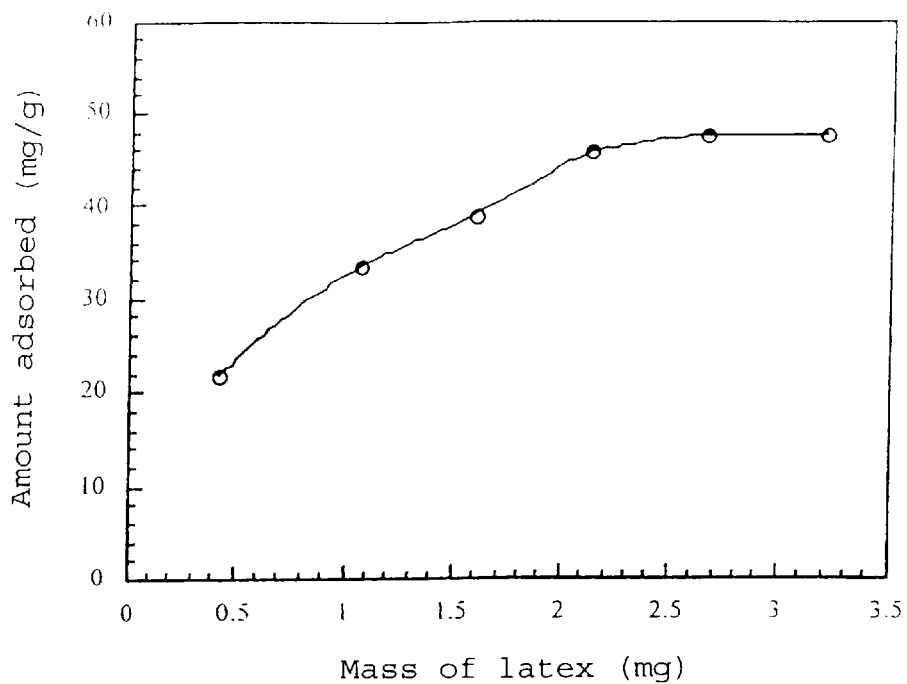

FIG. 5 shows that, for 0.14 mg of HSA and a latex of 2.1% solid content, a plateau of the amount adsorbed is reached for a volume of 0.125 ml of latex (i.e. 2.6 mg). This plateau corresponds to approximately 50 mg of proteins per gram of latex, i.e. presuming that the latex particles have a diameter in the vicinity of 1 mm and a density of 1.85 g/cm$^3$ ($\Sigma$=3.24 m$^2$/g): 15 mg of HSA per m$^2$ of polymer. This result is in the range expected.

It is thus this ratio (approximately 2 mg of latex for 0/1 mg of proteins) which will be used hereafter.

g. Results for the Adsorption

The optimized parameters for the adsorption are thus:

pH=4.7
Fi=0.01 mol/l
T=40° C.
t=10 min

D/ Desorption of the HSA Protein

The adsorption is carried out under the optimal conditions determined above, and then parameters which govern the desorption are studied.

The first desorption tests were carried out in eppendorf tubes. Firstly, the adsorption is performed under the conditions defined above (it is verified that virtually all of the proteins present in the medium are adsorbed). Next, the supernatant is drawn off, and then replaced with 1 ml of the solution the study of whose capacity to promote the desorption is desired.

After a variable desorption time, measurement of the optical density of this new supernatant makes it possible to deduce the amount of HSA desorbed, and thus the influence of the desorption time.

The desorption takes place to better effect at basic pH than at acid pH, and at 20° C. to better effect than at 40° C., which according to the influence of the pH and of the temperature was predictable. In addition, a short adsorption time (10 min) was chosen, because this time period is sufficient to adsorb virtually all of the proteins, and the more the proteins remain in contact with the latex, the less considerable is the desorption.

The influence of other parameters was less evident, and the results obtained are detailed below.

1—Influence of the Ionic Strength

Figure 6:
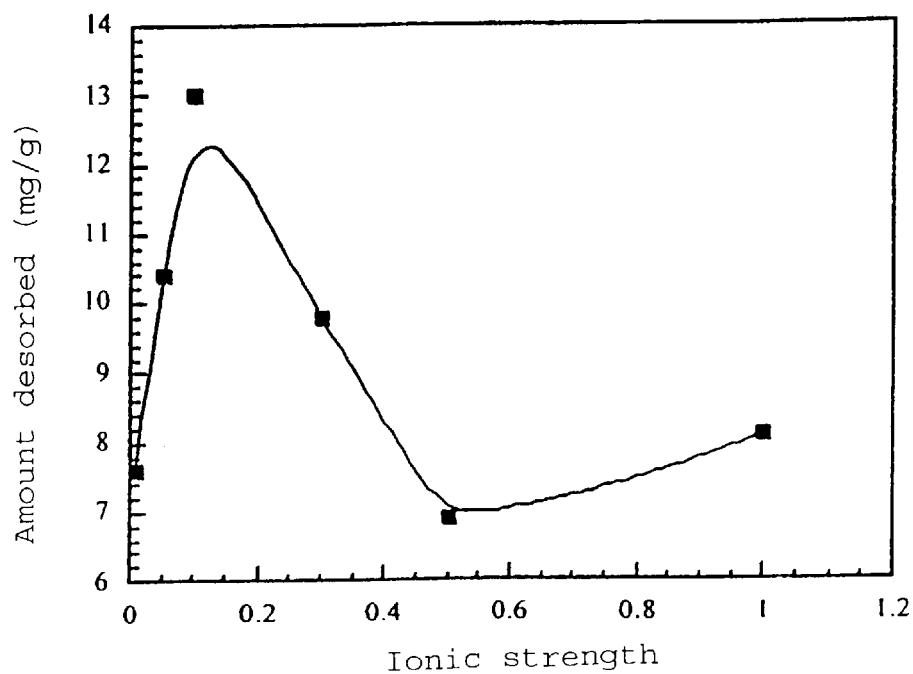

FIG. 6 shows the influence of the ionic strength of the buffer on the desorption.

This curve reveals the presence of a desorption maximum for an ionic strength close to 0.1 dmol.l$^{-1}$. This result is quite surprising. At basic pH, the latex and HSA are anionic, and thus the electrostatic forces are repulsive. In order to increase the desorption, they should not be screened; a priori, a low ionic strength is required. Conversely however, when the ionic strength increases, the furry coat of polyNIPAM finds itself in an incorrect solvent and thus contracts, and the proteins get closer together. Since they carry the same negative charge, the electrostatic repulsion leads to the desorption of a certain amount of proteins. The existence of two opposite influence phenomena justifies the existence of a maximum.

2—Influence of the Desorption Time

Figure 7:
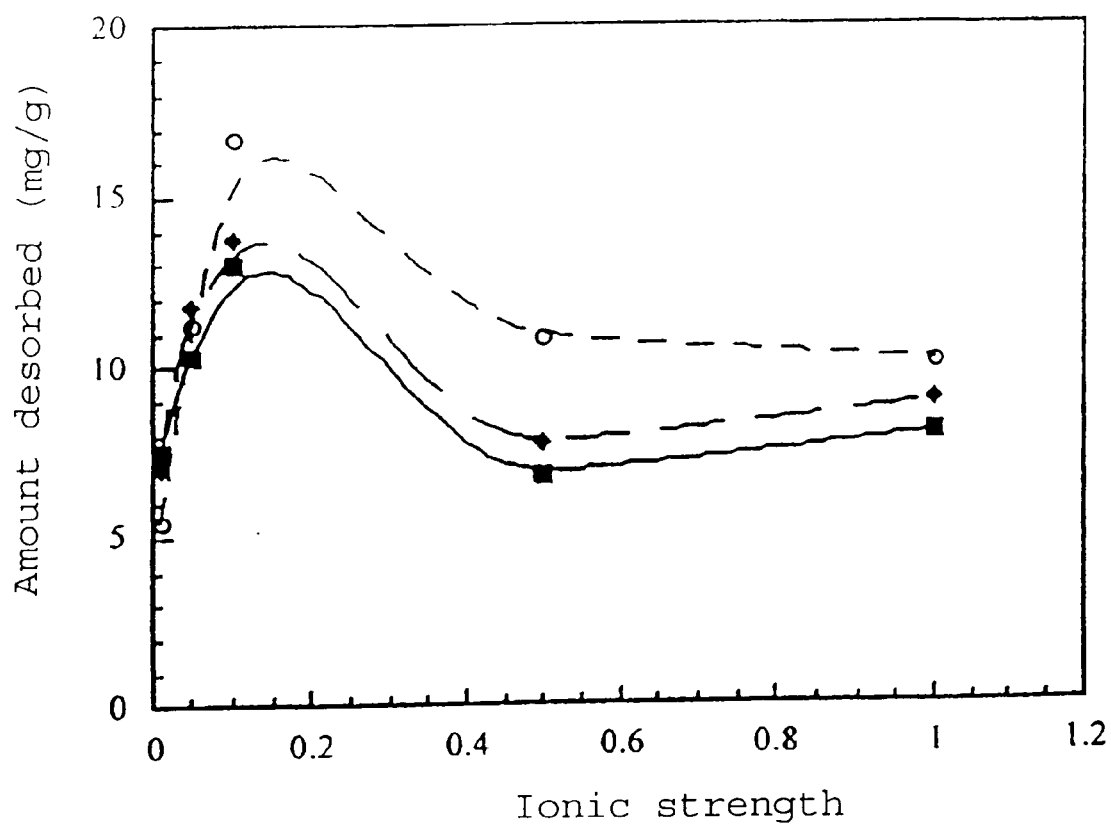

FIG. 7 shows that the amount desorbed increases slightly when the desorption time increases. A fairly short desorption time (2 h) was however chosen for practical reasons: thus, approximately 15% less than what might be obtained is desorbed.

3—Results for the Desorption

The optimized parameters for the desorption are thus:

pH>8.6
Fi=0.1 mol/l
T=20° C.
t>2 h

E/ Results: Concentration of Solutions Containing HSA

The adsorption is carried out for a total volume of 10 ml, under the optimal conditions, in "Falcon" tubes. For this, after preparing, in a buffer of pH=4.7 and of ionic strength 0.01 mol/l, an HSA solution with a concentration such that the concentration of proteins really in contact with the latex is 0.1 g.l$^{-1}$ taking into account the dilution, 27 mg of latex are introduced.

The amount adsorbed is approximately 0.095 mg.ml$^{-1}$ (i.e. 95% of the proteins initially present). After separation using a magnet, the desorption is then carried out by introducing 1 ml of buffer of pH=8.6, and then pH=10.8. The solution obtained has an HSA concentration equal to 0.23 mg.ml in the first case (24% of the amount adsorbed is desorbed), and 0.37 mg.ml$^{-1}$ in the second (39% is desorbed). The initial concentration may thus, under these conditions, be multiplied by a maximum of 3.7.

IV—Application to Urine

A/ General Comment

The preliminary studies were performed on an extremely simple medium: a single protein of known concentration in a buffered medium all the parameters of which have been determined.

Conversely, urine constitutes a very complex medium which contains several tens of proteins of different molecular weights, and which is rich in salts. However, to establish the protein concentration of the urine from the optical density, the calibration curves established for HSA were used; the results obtained are thus only qualitative. In addition, the pH and the protein concentration of the urine depends on the people and on their diet. It is thus necessary to determine these values for each batch of urine used.

B/ Results for the Urine of Negative Controls

The first series of experiments was carried out using the conditions of the preliminary tests. In the second series, certain steps were modified as a function of the results of the first series.

1—Procedure

After introducing the urine to be concentrated and 27 mg of latex into 10-ml "Falcon" tubes, the mixture is placed in a water-bath at 40° C. for a variable time. Next, the supernatant is drawn off, and then replaced with 1 ml of buffer at pH=4.7 which is removed almost instantaneously: the aim of this procedure is to wash the latex without, in principle, desorbing.

After adding 1 ml of buffer of pH=10.6 and ionic strength 0.01M, it is left to desorb at 20° C. for a time $t_D$. Bradford assaying the supernatant makes it possible to determine the total concentration of desorbed proteins.

2—Protein Assay (by Bradford)

The pH of the urine studied is in the vicinity of 7, and the initial protein concentration (for the batch used) is of the order of 0.02 g.l$^{-1}$. The analysis of the supernatants shows that:

1) it is necessary to acidify urine; at its natural pH which is close to 7, the adsorption does not reach 50% of the proteins present, whereas it approaches 80% in urine acidified at pH=4.6;
2) the washing step causes the loss of approximately 20% of the proteins adsorbed; this step was thus eliminated in the subsequent experiments.

The study of the influence of the adsorption time and of desorption shows that, unlike the results obtained in the preliminary study on HSA, it is necessary to adsorb for at least 60 min to reach the adsorption plateau. After a desorption time of 60 min in a volume of 1 ml, the solution obtained is 4 times more concentrated in proteins than the starting urine. This result is fairly satisfying since it is in agreement with the concentration assays for HSA alone, even though, in theory, it could be hoped to multiply the concentration by 10 since 10 ml are concentrated into 1 ml.

However, the final aim is not to concentrate all the proteins, but to isolate the protein of interest. Hence the value of analysing the various samples thus obtained on electrophoresis gel, to demonstrate the various protein(s).

V—Conclusions

A preliminary study made it possible to verify that the use of heat-sensitive magnetic latex particles makes it possible, by varying various physical parameters (pH, temperature, ionic strength), to adsorb and to desorb human albumin (HSA). It is thus possible, starting from a diluted 10 ml solution of this protein, to pass to a solution of 1 ml which is approximately 4 times more concentrated.

By optimizing the parameters, it is possible to adsorb up to 95% of the proteins. The fact that it is not possible to concentrate more is due to an incomplete desorption. In order to increase this degree of desorption, it is envisageable to add surfactants which are capable of exchanging with the adsorbed proteins.

The application of the optimal concentration conditions for HSA to urine makes it possible to obtain similar results. By desorbing in a suitable buffer, it is possible to multiply the protein concentration of a batch of urine by four. By freeze-drying the samples thus concentrated, a multiplication factor of 100 can be obtained, which is close to the degree of concentration obtained with the ammonium sulphate precipitation method. However, the solution obtained after freeze-drying is too concentrated in salts. A dialysis step would thus be necessary to replace the buffer of ionic strength 0.1 mol/l with a less saline medium, unless it is decided to desorb in a medium of almost zero ionic strength, even if it means desorbing only a smaller amount of proteins.

What is claimed is:

1. Heat-sensitive magnetic particle having a predetermined size between 0.05 and 10 μm, which comprises:
   an internal composite core which consists of a solid organic or inorganic particle, and which contains within itself a magnetic filler, and
   an external layer based on a polymer that interacts with at least one biological molecule, the external polymer is heat-sensitive and has a predetermined lower critical solubility temperature (LCST) between 10 and 100° C. characterized in that an intermediate layer is present between the internal core and the external layer, which isolates the magnetic filler of said internal core with respect to said functionalized external layer.

2. Particle according to claim 1, characterized in that the intermediate layer consists of at least:
   one functional or nonfunctional monomer that polymerizes in order to give a polymer, and
   one crosslinking agent.

3. Particle according to claim 1, characterized in that the external layer consists of at least:
   one functional monomer that polymerizes in order to give a polymer, and
   one initiator.

4. Particle according to claim 2, characterized in that the functional monomer consists of a cationic monomer.

5. Particle according to claim 2, characterized in that the functional monomer consists of an anionic monomer.

6. Particle according to claim 2, characterized in that the polymer consists of hydrophilic polymers.

7. Particle according to claim 2, characterized in that the crosslinking agent consists of N,N'-methylenebisacrylamide.

8. Particle according to claim 3, characterized in that the initiator consists of at least one cationic initiator.

9. Particle according to claim 3, characterized in that the initiator consists of at least one anionic initiator.

10. Particle according to claim 1, characterized in that the external layer is functionalized with a protonated amine or amidine group.

11. Particle according to claim 1, characterized in that the external layer is functionalized with a carboxylic or sulphate group.

12. Method for obtaining particles as defined according to claim 1, characterized in that it consists in:
   reacting a composite core which consists of a solid organic or inorganic particle, and which contains within itself a magnetic filler, and a functional or nonfunctional monomer that polymerizes in order to give a polymer constituting an intermediate layer around the internal composite core, and
   reacting a crosslinking agent to crosslink the polymer, and
   reacting the polymerized crosslinked intermediate layer with a functional monomer that polymerizes to give a polymer constituting an external layer.

13. Method for obtaining particles as defined according to claim 12, characterized in that the cationic magnetic particles are prepared by encapsulation by polymerization, on composite cores, of the water-soluble monomers of acrylamide and/or of acrylamide derivatives in the presence of azobis(2-amidinopropane)chloride.

14. Method according to claim 13, characterized in that the polymerization is performed in the presence of N,N'-methylenebisacrylamide and/or of 2-aminoethyl methacrylate chloride.

15. Method for obtaining particles as defined according to claim 12, characterized in that the anionic magnetic particles are prepared by encapsulation by polymerization, on composite cores, of the water-soluble monomers of acrylamide or of acrylamide derivatives in the presence of potassium persulphate.

16. Method according to claim 15, characterized in that the polymerization is performed in the presence of N,N'-methylenebisacrylamide and/or of carboxylic monomers.

17. Method according to claim 12, characterized in that the intermediate layer consists of at least one substance which isolates the magnetic filler.

18. Method according to claim 12, characterized in that it consists in using the reagents in a proportion of:

10 to 30% of water-soluble monomer of acrylamide or of an acrylamide derivative, at most 10% of at least one crosslinking agent, and 1 to 5% of at least one stabilizer, with respect to the total mass of the particle obtained by the method.

19. Use of cationic particles according to claim 1, to immobilize or extract nucleic acids or any polyelectrolytic entities, and to release and/or analyse, after magnetic separation, said nucleic acids or entities, the temperature of use being constantly lower than the LCST.

20. Use of anionic particles according to claim 1, to extract proteins by binding to the particles when the temperature is higher than the LCST, and to release and/or analyse, after magnetic separation, said proteins when the temperature is lower than the LCST.

21. Particle according to claim 1, characterized in that the predetermined lower critical solubility temperature (LCST) is between 20 and 60° C.

22. Particle according to claim 4, characterized in that the cationic monomer is 2-aminoethyl methacrylate chloride.

23. Particle according to claim 5, characterized in that the anionic monomer is a carboxylic or sulphate monomer.

24. Particle according to claim 6, characterized in that the hydrophilic polymers are acrylamine derivatives.

25. Particle according to claim 6, characterized in that the hydrophilic polymers are poly(NIPAM) obtained by polymerization of N-isopropylacrylamide (NIPAM).

26. Particle according to claim 8, characterized in that the at least one cationic initiator is azobis(2-amidinopropane) chloride.

27. Particle according to claim 9, characterized in that the at least one anionic initiator is potassium persulphate.

28. Method according to claim 17, characterized in that the at least one substance is polystyrene and/or methyl polymethacrylate.

* * * * *